(12) United States Patent
Miura

(10) Patent No.: US 6,672,140 B2
(45) Date of Patent: Jan. 6, 2004

(54) METHOD FOR MEASURING VISCOSITY OF LIQUID, AND METHOD AND APPARATUS FOR MEASURING VISCO-ELASTICITY OF LIQUID

(75) Inventor: Shinsuke Miura, Shizuoka-ken (JP)

(73) Assignee: CBC Materials Co., Ltd., Tokyo (JP)

( * ) Notice: Subject to any disclaimer, the term of this patent is extended or adjusted under 35 U.S.C. 154(b) by 14 days.

(21) Appl. No.: 09/814,965

(22) Filed: Mar. 23, 2001

(65) Prior Publication Data

US 2002/0007665 A1 Jan. 24, 2002

(30) Foreign Application Priority Data

May 9, 2000 (JP) .................................. 2000-135722

(51) Int. Cl.⁷ .............................................. G01N 11/00
(52) U.S. Cl. .................................................... 73/54.25
(58) Field of Search ........................... 73/54.25, 54.24; 106/18.11, 711; 310/323.11, 333; 702/54

(56) References Cited

U.S. PATENT DOCUMENTS

| | | | | |
|---|---|---|---|---|
| 3,554,263 A | * | 1/1971 | Bachmann | 159/6.2 |
| 4,292,673 A | * | 9/1981 | Du Bae | 702/54 |
| 4,341,111 A | | 7/1982 | Husar | |
| 4,488,427 A | * | 12/1984 | Matusik et al. | 73/54.23 |
| 4,721,874 A | * | 1/1988 | Emmert | 310/333 |
| 4,754,640 A | * | 7/1988 | Fitzgerald et al. | 73/32 A |
| 4,811,593 A | * | 3/1989 | Miura et al. | 73/54.26 |
| 4,862,384 A | * | 8/1989 | Bujard et al. | 702/54 |
| 4,892,396 A | * | 1/1990 | Kushibiki et al. | 359/676 |
| 4,905,499 A | * | 3/1990 | Miura et al. | 73/32 A |
| 4,978,580 A | * | 12/1990 | Tezuka et al. | 428/484 |
| 5,167,710 A | * | 12/1992 | Leroux et al. | 106/711 |
| 5,201,215 A | * | 4/1993 | Granstaff et al. | 73/54.41 |
| 5,448,129 A | * | 9/1995 | Sumihara et al. | 310/323.11 |
| 5,698,773 A | * | 12/1997 | Blom et al. | 73/54.18 |
| 5,750,884 A | * | 5/1998 | Field | 73/54.24 |
| 5,779,775 A | * | 7/1998 | Kuwabara et al. | 106/18.11 |
| 5,833,764 A | * | 11/1998 | Rader et al. | 134/22.11 |
| 5,847,267 A | * | 12/1998 | Janzen | 73/54.01 |
| 6,289,734 B1 | * | 9/2001 | Daugela | 73/573 |

FOREIGN PATENT DOCUMENTS

| | | |
|---|---|---|
| GB | 2 071 324 | 9/1981 |
| GB | 2 202 944 | 10/1988 |
| GB | 2 281 621 | 3/1995 |
| JP | 5-20692 | 3/1993 |

OTHER PUBLICATIONS

Malvino, Albert, Electronic Principles, 1984, McGraw–Hills, ISBN 0–07–039912–3.*

* cited by examiner

Primary Examiner—Hezron Williams
Assistant Examiner—Jay L Politzer
(74) Attorney, Agent, or Firm—Wenderoth, Lind & Ponack, L.L.P.

(57) ABSTRACT

A method for measuring viscosity of liquid, in which a liquid detecting piece 3 is vibrated by a vibrator 1, vibration of the liquid detecting piece 3 in liquid 4 is detected, and viscosity of the liquid 4 is measured from vibration thus obtained, the method comprising the steps of detecting frequency and amplitude which are variable attributable to liquid-specific visco-elasticity from the vibration, obtaining impedance of the liquid from the frequency and the amplitude, and obtaining a dynamic viscosity from a real number part and an imaginary number part of the impedance. There is also disclosed a method for measuring visco-elasticity of liquid comprising the step of obtaining a dynamic viscosity, a dynamic elasticity and a static elasticity of the liquid from a real number part and an imaginary number part of the impedance. There is also disclosed an apparatus comprising a vibration-type liquid detecting apparatus U for performing the viscosity measurement and the visco-elasticity measurement, a frequency/amplitude detecting circuit 7, 8, an impedance computing circuit 9, a circuit 10a for computing a dynamic viscosity and a dynamic elasticity of the liquid and a circuit 10b for computing a static viscosity of the liquid.

16 Claims, 2 Drawing Sheets

METHOD FOR MEASURING VISCOSITY OF LIQUID, AND METHOD AND APPARATUS FOR MEASURING VISCO-ELASTICITY OF LIQUID

BACKGROUND OF THE INVENTION

1. Field of the Invention

This invention relates to a method for measuring viscosity of liquid, and a method and an apparatus for measuring visco-elasticity of liquid, in which viscosity and visco-elasticity of liquid to be measured can be obtained correctly using a vibration-type liquid detecting apparatus.

2. Related Art

A vibration-type liquid detecting apparatus U as represented by Japanese Patent Publication No. H05-20692 employs, as shown in FIG. 2, a method for measuring viscosity of liquid, in which vibration of a piezoelectric vibrator 1 composed of a piezoelectric element is transmitted to a liquid detecting piece 3 through a vibration transmission shaft 2 so as to be resonated, the liquid detecting piece 3 is immersed and vibrated in liquid 4 to be measured so that it can detect viscous resistance of the liquid, and then amplitude of the vibration corresponding to the viscous resistance is detected by an angular acceleration sensor 5 composed of a piezoelectric element disposed at an end of the vibration transmission shaft 2.

Specifically, a curve of a static viscosity (viscous property)-to-amplitude of vibration in a plurality of viscosity standard liquids (Newtonian liquid defined in JIS) is obtained beforehand. On the other hand, an actual amplitude of vibration of liquid to be measured is obtained. Then, a viscosity corresponding to the amplitude on the curve of the static viscosity (viscous property)-to-amplitude is regarded as the viscosity of the liquid to be measured. In other words, it employs a method in which the amplitude is regarded as a variable determining the viscosity.

As mentioned above, a static viscosity is obtained from vibration of a liquid detecting piece in liquid and the viscosity thus obtained is used as a viscosity of the liquid. This measuring method can be the correct method, only on the assumption that the liquid to be measured, such as water, gasoline, oil and the like which is generally handled as Newtonian liquid is a liquid truly equivalent to the Newtonian liquid.

On the other hand, a polymeric solution such as a photosensitive agent and a liquid enriched with visco-elasticity such as a coating material for paper are also regarded as Newtonian liquid and the measuring method based on the Newtonian liquid is applied thereto. However, since those liquids are enriched with visco-elasticity which is not expected in the Newtonian liquid, it is hard to say that the viscosity obtained according to the aforementioned measuring method reflects an actual viscosity correctly.

As a result of repeated measurement of viscosity of the non-Newtonian liquid and the Newtonian liquid utilizing a liquid detecting piece having various resonant frequencies, the inventor of the present invention has found out that the dynamic viscosity detected by vibration of the liquid detecting piece is an important element as an element for measuring viscosity and visco-elasticity of liquid, the dynamic viscosity in those liquids is not necessarily equivalent to the static viscosity, a difference between the dynamic viscosity and the static viscosity becomes more significant as the frequency of vibration is increased (dynamic viscosity is highly dependent on frequency), and therefore, the dynamic viscosity reflects viscosity and visco-elasticity through frequency.

SUMMARY OF THE INVENTION

Based on the above finding, there is provided a method for measuring viscosity or visco-elasticity in which a liquid detecting piece is vibrated by a vibrator, vibration in the liquid is detected, and viscosity or elasticity of the liquid is measured from vibration thus obtained, the method comprising the steps of detecting frequency and amplitude which are variable attributable to liquid-specific visco-elasticity from the vibration, obtaining impedance of the liquid from the frequency and the amplitude, and obtaining a dynamic viscosity or a dynamic elasticity from a real number part and an imaginary number part of the impedance.

The method may comprise the steps of detecting frequency and amplitude which are variable attributable to liquid-specific visco-elasticity from the vibration, obtaining impedance of the liquid from the frequency and the amplitude, and obtaining a dynamic viscosity, a dynamic elasticity and a static elasticity of the liquid from a real number part and an imaginary number part of the impedance.

By the above-mentioned method, there can correctly be obtained a viscosity and a visco-elasticity of various kinds of liquid to be measured ranging from a liquid having no visco-elasticity and to a liquid enriched with visco-elasticity in a case in which a vibration-type liquid detecting apparatus having such a reciprocal vibration mode as a circular direction vibration.

From another aspect of the present invention, there is also provided an apparatus for measuring visco-elasticity of liquid comprising a liquid detecting piece resonated in liquid serving a vibrator as a drive source, a circuit for detecting frequency of vibration of the liquid detecting piece in the liquid, a circuit for detecting amplitude of the vibration, a circuit for computing impedance of the vibrator from the frequency and the amplitude of the vibration, and a circuit for computing a dynamic viscosity, a dynamic elasticity and a static viscosity of the liquid from a real number and an imaginary number of the impedance computed by the impedance computing circuit.

Particularly, according to the present invention, there are provided a measuring method and an apparatus, in which visco-elastic properties (viscosity and elasticity) of liquid, which directly affects the physical properties of such polymeric solutions as silicon oil and synthetic resin liquid as a raw material of synthetic resin products, can easily be measured accurately and in real time.

DETAILED DESCRIPTION OF THE EMBODIMENT

Figure 2:
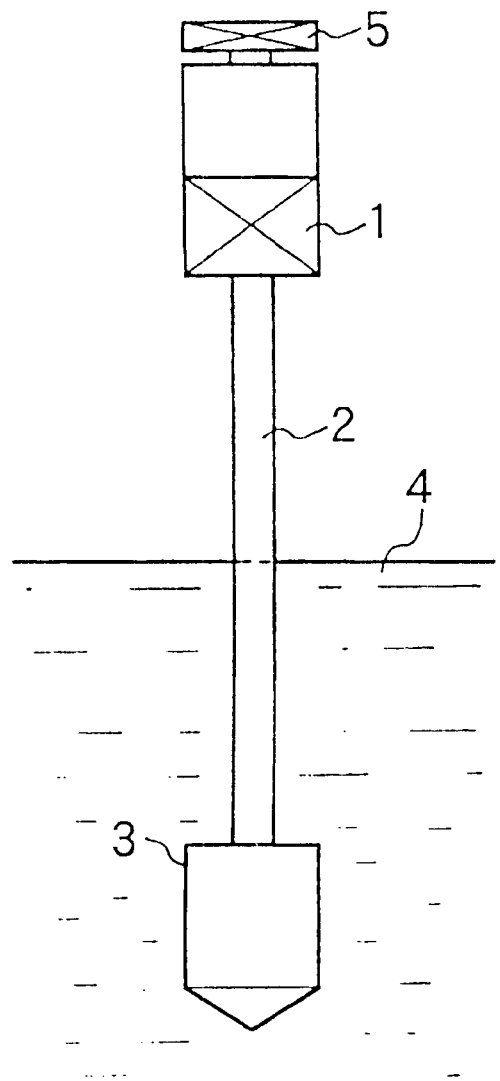
FIG. 2 is a side view schematically showing the vibration-type liquid detecting apparatus.

According to one embodiment of the present invention, there is employed a method for measuring viscosity. In this method, a vibrator 1 of FIG. 2, which is composed of a piezoelectric element as an electromechanical means, or a vibrator 1, not shown, which is composed of a magneto-mechanical converting means which vibrates a liquid detecting piece 3 by magnetic force and the liquid detecting piece 3 are directly connected to each other on a line where their vibrating axes are aligned, through a vibration transmission shaft 2. Then, the vibration of the vibrator 1 is transmitted for resonance to the liquid detecting piece 3 through the vibration transmission shaft 2. That is to say, by using a measuring method for resonating the three component members 1, 2, 3 at a prescribed resonant frequency, the liquid detecting piece 3 is immersed and vibrated (resonance) in liquid 4 to be measured so that the liquid detecting piece 3 detects a viscous resistance of the liquid. Then, the amplitude and frequency of the vibration corresponding to the viscous resistance are detected by an angular acceleration sensor 5 which is composed of a piezoelectric element and which is disposed at an end opposite to the liquid detecting piece 3 of the transmission shaft 2, thereby measuring viscosity of the liquid.

The vibrator 1, the vibration transmission shaft 2, the liquid detecting piece 3 and the angular acceleration sensor 5 constitute a vibration-type liquid detecting apparatus U. A vibrating mode of the vibrator 1 vibrated by this vibration-type liquid detecting apparatus U is a resonance in a circular direction vibration mode reciprocally moved, at a predetermined angle of rotation, on a circular locus about the above-mentioned axis.

The liquid detecting piece 3 is vibrated (resonance) by the vibrator 1 and variation of the vibration (resonance) in the liquid 4 of the liquid detecting piece 3 is detected. And viscosity of the liquid 4 is measured from variation of the vibration. In this viscosity measuring method, a dynamic viscosity of the liquid 4 is obtained from the frequency and amplitude of the varied vibration (resonance) and the viscosity of the liquid 4 is obtained therefrom.

As an example of development, there is provided a method for measuring visco-elasticity of liquid, in which a liquid detecting piece 3 is vibrated (resonance) by a vibrator 1, variation of vibration (resonance) of the liquid detecting piece 3 in liquid 4 is detected, and viscosity and elasticity of the liquid 4 is measured from the variation of vibration thus obtained, wherein a dynamic viscosity of the liquid 4 is obtained from the frequency and amplitude of the varied vibration, then, a dynamic viscosity of the liquid 4 is obtained from the frequency and amplitude, and then and a visco-elasticity of the liquid 4 is obtained therefrom.

As another example of development, there is provided a method for measuring visco-elasticity of a liquid 4, in which a liquid detecting piece 3 is vibrated (resonance) by a vibrator 1, variation of vibration (resonance) of the liquid detecting piece 3 in the liquid 4 is detected, and viscosity and elasticity of the liquid 4 is detected from the variation of vibration thus obtained, wherein a dynamic viscosity of the liquid is obtained from frequency and amplitude of the varied vibration, a static viscosity is obtained from the dynamic viscosity and the dynamic elasticity, and then, viscosity and elasticity of the liquid 4 is obtained therefrom.

Figure 1:
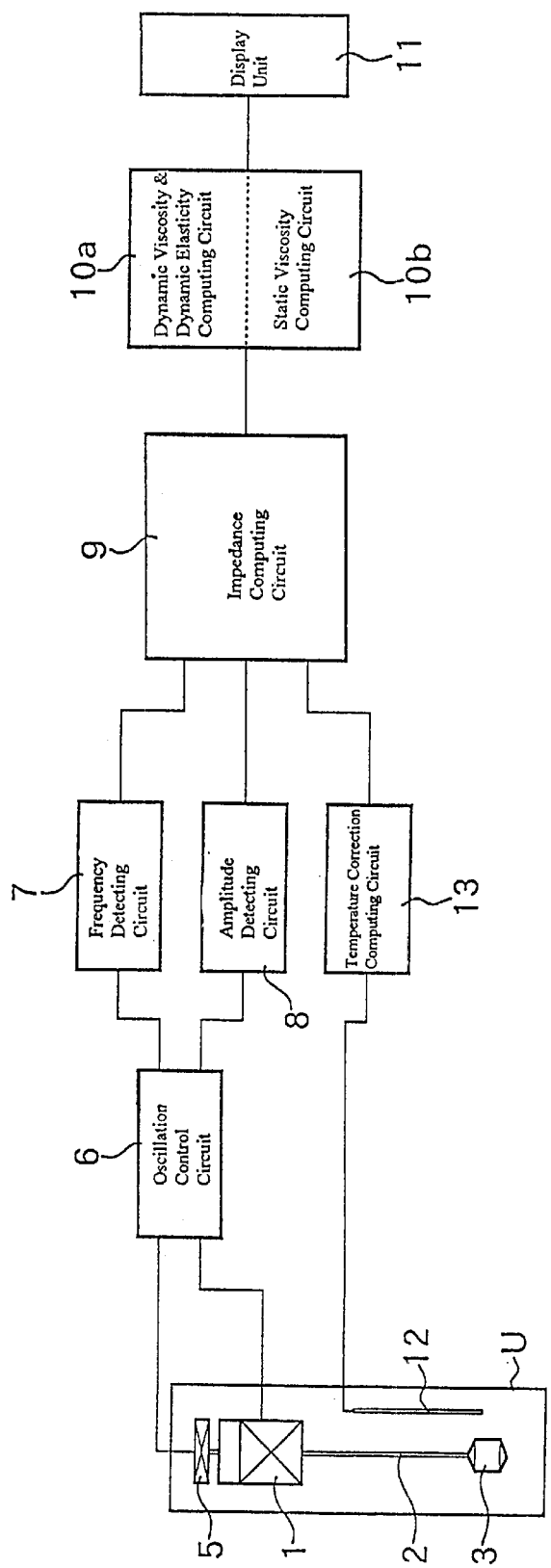
FIG. 1 is a circuit block diagram for executing a method for measuring viscosity of liquid and a method for measuring visco-elasticity of liquid using a vibration-type liquid detecting apparatus.

An example of a circuit of the method for measuring viscosity of liquid and the method for measuring visco-elasticity of liquid will now be described with reference to FIG. 1.

A frequency detecting circuit 7 for detecting a resonance frequency and an amplitude detecting circuit 8 for detecting an amplitude in the resonance frequency are connected to the vibrator 1 and the angular acceleration sensor 5 in parallel relation through an oscillation control circuit 6.

Moreover, an impedance computing circuit 9 for computing an impedance of the vibrator 1 from the frequency and the amplitude in the vibration is connected to the frequency detecting circuit 7 and the amplitude detecting circuit 8, and a dynamic viscosity & dynamic elasticity computing circuit 10*a* and a static viscosity computing circuit 10*b* are connected to the impedance computing circuit 9.

The impedance computing circuit 9 computes a real number part and an imaginary number part of the impedance of the vibrator 1 and then the computing circuits 10*a*, 10*b* compute the dynamic viscosity and the dynamic elasticity from the computation of the impedance computing circuit 9. The results of computation are displayed in a display unit 11.

The oscillation control circuit 6 is composed of a phase lock circuit (PLL). This oscillation control circuit 6 compares a phase of a drive voltage signal of the vibrator 1 with that of an angular acceleration sensor 5 in the case where the liquid detecting piece 3 is immersed and resonated in various liquids 4 corresponding to the Newtonian liquid and non-Newtonian liquid and controls such that their phases are normally maintained in a predetermined phase difference. That is to day, the oscillation control circuit 6 controls oscillation such that the vibrator 1 is normally resonated at a resonance frequency at the time when the liquid detecting piece 3 is immersed in the liquid 4.

Moreover, the vibration-type liquid detecting apparatus U is integrally equipped with a temperature sensor 12 so that when the liquid detecting piece 4 is immersed in the liquid 4, the temperature sensor 12 is simultaneously immersed therein. A temperature detected by the temperature sensor 12 is input into a temperature correction computing circuit 13. This temperature correction computing circuit 13 is connected to the impedance computing circuit 9 so that a correction value computed by the temperature correction computing circuit 13 is provided as a computing value in the impedance computing circuit 9. Then, in this impedance computing circuit 9, the impedance at the temperature at that time is correctly computed and the computed values are output to the dynamic viscosity and dynamic elasticity computing circuit 10*a* and the static viscosity computing circuit 10*b* and displayed in the display unit 11.

The above-described method for measuring a viscosity of liquid and method for measuring a visco-elasticity of liquid will be described hereinafter in more detail with reference to numerical expressions 1 to 9.

$$D = \frac{f_0 - f}{f_0}$$ Numerical Expression 1

$$X = \left\{ \frac{4D}{K(2-D)} \right\}^2$$ Numerical Expression 2

$$R = \left\{ \frac{V_0}{V}(x + \sqrt{N}) - x \right\}^2 \cdot \frac{1}{1-D}$$ Numerical Expression 3

$$\eta = \frac{1}{\rho} \cdot \sqrt{RX}$$ Numerical Expression 4

$$G = \frac{\omega}{2\rho} \cdot (R - X)$$ Numerical Expression 5

$$\omega = 2\pi f$$

$$Y = \frac{R - X}{R + X}$$ Numerical Expression 6

$$T = \sqrt{\frac{Y^2}{1 - Y^2}} = \frac{G}{\omega \eta}$$ Numerical Expression 7

-continued $$\eta 0 = \frac{2}{\rho} \cdot \frac{RT}{Y(1+Y)}$$ Numerical Expression 8

$$= \eta(1+T^2) = \frac{G}{\omega} \cdot \frac{1+T^2}{T}$$

$$\eta' = \eta - j\frac{G}{\omega}$$ Numerical Expression 9

<Explanation of Numerical Expression 1>

The vibrator 1 driven by the oscillation control circuit 6 is resonated at a resonance frequency f in the liquid 4 and outputs an electric signal V.exp (j2πft) to the frequency detecting circuit 7 and the amplitude detecting circuit 8. Reference character j denotes a unit imaginary number. The frequency detecting circuit 7 detects the resonance frequency f from that signal and inputs it into the impedance computing circuit 9.

Similarly, the amplitude detecting circuit 8 detects the vibration amplitude in the resonance frequency f as a voltage value and outputs it to the impedance computing circuit 9.

A frequency deviation D is computed from a resonance frequency f0 in air (a state not immersed in the liquid 4) and the resonance frequency f in the liquid 4, which are preliminarily stored in the impedance computing circuit 9.

<Explanation of Numerical Expression 2>

By using the frequency deviation value D obtained according to the numerical expression 1 and a specific constant K determined by dimension, etc. of the vibrator 1, which is preliminarily stored in the impedance computing circuit 9, the imaginary number part of the impedance of the vibrator 1 is computed as a value X which is proportional to the square of the imaginary number part.

<Explanation of Numeral Expression 3>

Similarly, by using a specific constant N determined by the viscosity of a viscosity standard liquid and a physical value of the viscosity standard liquid, such as the density of the viscosity standard liquid, as established by JIS or ANSI, which are preliminarily stored in the impedance computing circuit 9, a voltage value V0 at the time of being immersed in the viscosity standard liquid, a value x, as a constant, which is specific to the vibrator 1 and proportional to an internal resistance of the vibration-type detecting apparatus U, the voltage value V and the frequency deviation value D obtained according to the numerical expression 1, a real number part of the impedance is computed as a value R which is proportional to the square of the real number part.

<Explanation of Numerical Expressions 4 and 5>

A value R corresponding to the real number part obtained according to the above numerical expression 3 and a value X corresponding to the imaginary number part obtained according to the numerical expression 2 are given inputted to the computing circuit 10a for computing a dynamic viscosity and a dynamic elasticity so that a dynamic viscosity η and a dynamic elasticity G are computed according to the numerical expressions 4 and 5, respectively. The reference character ω denotes the resonance angular frequency and is in such a relation to the resonance frequency f as being shown by the lower-listed expression in the numerical expression 5. The reference character ρ denotes density of the liquid.

<Explanation of Numerical Expressions 6, 7 and 8>

On the other hand, in the static viscosity computing circuit 10b, by using a value R which is proportional to square of the real number part of impedance obtained according to numerical expression 3, and a value X which is proportional to the square of the imaginary number part of impedance obtained according to numerical expression 2, a value Y, as a sine of a phase angles, and a value T, as a tangent (tan) of a phase angle, are computed according to the numerical expressions 6 and 7, respectively. Then, by using those values (R, Y, T), a static viscosity η0 is computed according to the numerical expression 8. Otherwise, by using the dynamic viscosity η and the dynamic elasticity G obtained according to the numerical expressions 4 and 5, respectively, and T obtained by the numerical expression 7, a static viscosity η0 is computed according to the numerical expression 8.

<Explanation of Numerical Expression 9>

The display unit 11 displays the dynamic viscosity η, the dynamic elasticity G and a static viscosity η0. The display unit 11 further displays the viscosity (complex elasticity) η' obtained according to the numerical expression 9 and the value T as a tan of the chase angle.

The temperature detected by the temperature sensor 12 is input into the temperature correction computing circuit 13. This temperature correction computing circuit 13 is connected to the impedance computing circuit 9, and a correction value computed by the temperature correction computing circuit 13 is provided as a computation value in the impedance computing circuit 9. Then, the above impedance at a temperature at that time is correctly computed by the impedance computing circuit 9 and the result of computation is output to the circuit 10a for computing a dynamic viscosity and a dynamic elasticity of the liquid and the circuit 10b for computing a static viscosity of the liquid.

The temperature correction computing circuit 13 is adapted to detect an error caused by thermal expansion and contraction of the liquid detecting piece 3 which is caused by temperature as a factor of variation of the resonance frequency and to correct it. The output of this computing circuit 13 is input into the impedance computing circuit 9 so as to be used as a correction value of the computation value according to the numerical expressions 1 to 9.

The value obtained by measuring viscosity of a liquid by operating the liquid detecting piece in a non-vibration mode (there is no concept of frequency as in the case where the liquid detecting piece is vibrated at a predetermined frequency) as in the case where the liquid detecting piece is rotated in a predetermined direction is referred to as a static viscosity. Through measurement in the non-vibration mode, the visco-elastic property of the liquid cannot be obtained.

On the other hand, the viscosity obtained by measuring a viscosity by operating the liquid detecting piece in a vibration mode having a predetermined frequency is referred to as a dynamic viscosity. The present invention intends to measure not only the dynamic viscosity and dynamic elasticity but also the static viscosity from the frequency and amplitude detected by operating the liquid detecting piece in a vibration mode as later described.

The Newtonian liquid such as water and gasoline has equal dynamic viscosity and static viscosity. On the other and hand in the non-Newtonian liquid such as a polymeric solution, the dynamic viscosity and static viscosity are not equal to each other but the dynamic viscosity is varied in value when the frequency is varied. This proves that the polymeric solution has a viscous property. That is to say, the polymeric solution has all of the properties of static viscosity, dynamic viscosity and dynamic elasticity.

According to the present invention, there can be provided a method for measuring viscosity of liquid, a method for measuring visco-elasticity of liquid and an apparatus for carrying out the methods in which a viscosity and a visco-elasticity of various kinds of liquid to be measured ranging from liquid having no visco-elasticity to liquid having enriched visco-elasticity can be obtained correctly.

Particularly, in such polymeric solutions as silicon oil and synthetic resin liquid as a raw material of synthetic resin products, the visco-elastic property (dynamic viscosity and dynamic elasticity) of liquid directly affects the physical properties and therefore, an accurate measurement is required. The present invention can properly meet with this requirement.

What is claimed is:

1. An apparatus for measuring visco-elasticity of liquid, said apparatus comprising:

a transmission shaft;

a liquid detecting piece located on said transmission shaft, wherein said liquid detecting piece is to be immersed into the liquid;

a vibrator located on said transmission shaft such that a vibration axis of said vibrator aligns with a vibration axis of said liquid detecting piece and a longitudinal axis of said transmission shaft, wherein vibration of said vibrator is transmitted to said liquid detecting piece through said transmission shaft such that said vibrator, said transmission shaft, and said liquid detecting piece resonate about the longitudinal axis of said transmission shaft;

a sensor located on said transmission shaft operable to detect amplitude and frequency of vibration of said liquid detecting piece;

an oscillation control circuit, connected to said vibrator and said sensor, operable to output a driving signal for driving said vibrator at a frequency that causes a predetermined phase difference between the driving signal and the detected vibration, and to output a frequency signal including information of the amplitude and the frequency of the vibration detected by said sensor at a time of measurement;

a circuit operable to detect the frequency of the vibration of said liquid detecting piece in the liquid from the signal outputted from said oscillation control circuit;

a circuit operable to detect the amplitude of the vibration from the signal outputted from said oscillation control circuit;

a circuit operable to compute impedance of said vibrator from the detected frequency and amplitude of the vibration; and a computing circuit operable to compute a dynamic viscosity and a dynamic elasticity of the liquid from a real number part and an imaginary number part of the impedance computed by said impedance computing circuit.

2. An apparatus according to claim 1, wherein said sensor comprises a piezoelectric element.

3. An apparatus according to claim 1, wherein said computing circuit is further operable to compute a static viscosity of the liquid from the dynamic viscosity and the dynamic elasticity computed by said computing circuit.

4. An apparatus according to claim 1, wherein the detected amplitude of the vibration is detected as a voltage value.

5. An apparatus for measuring visco-elasticity of liquid, said apparatus comprising:

a transmission shaft;

a liquid detecting piece located on said transmission shaft, wherein said liquid detecting piece is to be immersed into the liquid;

a vibrator located on said transmission shaft such that a vibration axis of said vibrator aligns with a vibration axis of said liquid detecting piece and a longitudinal axis of said transmission shaft, wherein vibration of said vibrator is transmitted to said liquid detecting piece through said transmission shaft such that said vibrator, said transmission shaft, and said liquid detecting piece resonate about the longitudinal axis of said transmission shaft;

a sensor located on said transmission shaft operable to detect amplitude and frequency of vibration of said liquid detecting piece;

an oscillation control circuit, connected to said vibrator and said sensor, operable to output a driving signal for driving said vibrator at a frequency that causes a predetermined phase difference between the driving signal and the detected vibration, and to output a including information of the amplitude and the frequency of the vibration detected by said sensor at a time of measurement;

a circuit operable to detect the frequency of the vibration of said liquid detecting piece in the liquid from the signal outputted from said oscillation control circuit;

a circuit operable to detect the amplitude of the vibration from the signal outputted from said oscillation control circuit;

a circuit operable to compute impedance of said vibrator from the detected frequency and amplitude of the vibration;

a first computing circuit operable to compute a dynamic viscosity and a dynamic elasticity of the liquid from a real number part and an imaginary number part of the impedance computed by said impedance computing circuit; and a second computing circuit operable to compute a static viscosity of the liquid from the impedance computed by said impedance computing circuit.

6. An apparatus according to claim 5, wherein said sensor comprises a piezoelectric element.

7. An apparatus according to claim 5, wherein said second computing circuit is further operable to compute a static viscosity of the liquid from the dynamic viscosity and the dynamic elasticity computed by said first computing circuit.

8. An apparatus according to claim 5, wherein the detected amplitude of the vibration is detected as a voltage value.

9. An apparatus for measuring visco-elasticity of liquid, said apparatus comprising:

a temperature sensor, to be immersed into the liquid, operable to detect temperature of the liquid;

a temperature correction computing circuit operable to compute a correction value of temperature based on the temperature detected by said temperature sensor;

a transmission shaft;

a liquid detecting piece located on said transmission shaft, wherein said liquid detecting piece is to be immersed into the liquid;

a vibrator located on said transmission shaft such that a vibration axis of said vibrator aligns with a vibration axis of said liquid detecting piece and a longitudinal axis of said transmission shaft, wherein vibration of said vibrator is transmitted to said liquid detecting piece through said transmission shaft such that said vibrator, said transmission shaft, and said liquid detecting piece resonate about the longitudinal axis of said transmission shaft;

a sensor located on said transmission shaft operable to detect amplitude and frequency of vibration of said liquid detecting piece;

an oscillation control circuit, connected to said vibrator and said sensor, operable to output a driving signal for driving said vibrator at a frequency that causes a predetermined phase difference between the driving signal and the detected vibration, and to output a signal including information of the amplitude and the frequency of the vibration detected by said sensor at a time of measurement;

a circuit operable to detect the frequency of the vibration of said liquid detecting piece in the liquid from the signal outputted from said oscillation control circuit;

a circuit operable to detect the amplitude of the vibration from the signal outputted from said oscillation control circuit;

a circuit operable to compute impedance of said vibrator from the detected frequency and amplitude of the vibration and the correction value computed by said temperature correction computing circuit; and a computing circuit operable to compute a dynamic viscosity and a dynamic elasticity of the liquid from a real number part and an imaginary number part of the impedance computed by said impedance computing circuit.

10. An apparatus according to claim 9, wherein said sensor comprises a piezoelectric element.

11. An apparatus according to claim 9, wherein said computing circuit is further operable to compute a static viscosity of the liquid from the dynamic viscosity and the dynamic elasticity computed by said computing circuit.

12. An apparatus according to claim 9, wherein the detected amplitude of the vibration is detected as a voltage value.

13. An apparatus for measuring visco-elasticity of liquid, said apparatus comprising:

a temperature sensor, to be immersed into the liquid, operable to detect temperature of the liquid;

a temperature correction computing circuit operable to compute a correction value of temperature based on the temperature detected by said temperature sensor;

a transmission shaft;

a liquid detecting piece located on said transmission shaft, wherein said liquid detecting piece is to be immersed into the liquid;

a vibrator located on said transmission shaft such that a vibration axis of said vibrator aligns with a vibration axis of said liquid detecting piece and a longitudinal axis of said transmission shaft, wherein vibration of said vibrator is transmitted to said liquid detecting piece through said transmission shaft such that said vibrator, said transmission shaft, and said liquid detecting piece resonate about the longitudinal axis of said transmission shaft;

a sensor located on said transmission shaft operable to detect amplitude and frequency of vibration of said liquid detecting piece;

an oscillation control circuit, connected to said vibrator and said sensor, operable to output a driving signal for driving said vibrator at a frequency that causes a predetermined phase difference between the driving signal and the detected vibration, and to output a signal including information of the amplitude and the frequency of the vibration detected by said sensor at a time of measurement;

a circuit operable to detect the frequency of vibration of said liquid detecting piece in the liquid from the signal outputted from said oscillation control circuit;

a circuit operable to detect the amplitude of the vibration from the signal outputted from said oscillation control circuit;

a circuit operable to compute impedance of said vibrator from the correction value computed by said temperature correction computing circuit and the detected frequency and amplitude of the vibration;

a first computing circuit operable to compute a dynamic viscosity and a dynamic elasticity of the liquid from a real number part and an imaginary number part of the impedance computed by said impedance computing circuit; and a second computing circuit operable to compute a static viscosity of the liquid from the impedance computed by said impedance computing circuit.

14. An apparatus according to claim 13, wherein said sensor comprises a piezoelectric element.

15. An apparatus according to claim 13, wherein said second computing circuit is further operable to compute a static viscosity of the liquid from the dynamic viscosity and the dynamic elasticity computed by said first computing circuit.

16. An apparatus according to claim 13, wherein the detected amplitude of the vibration is detected as a voltage value.

* * * * *